(12) United States Patent
Vonk

(10) Patent No.: US 6,658,293 B2
(45) Date of Patent: Dec. 2, 2003

(54) METHOD AND SYSTEM FOR ATRIAL CAPTURE DETECTION BASED ON FAR-FIELD R-WAVE SENSING

(75) Inventor: Ben F. M. Vonk, Wehl (NL)

(73) Assignee: Medtronic, Inc., Minneapolis, MN (US)

( * ) Notice: Subject to any disclaimer, the term of this patent is extended or adjusted under 35 U.S.C. 154(b) by 230 days.

(21) Appl. No.: 09/842,882

(22) Filed: Apr. 27, 2001

(65) Prior Publication Data
US 2002/0183798 A1 Dec. 5, 2002

(51) Int. Cl.$^7$ ............................................. A61N 1/365
(52) U.S. Cl. .................................................... 607/28
(58) Field of Search ................... 607/28, 27, 9, 607/62; 600/521

(56) References Cited

U.S. PATENT DOCUMENTS

| | | |
|---|---|---|
| 4,316,472 A | 2/1982 | Mirowski et al. |
| 4,379,459 A | 4/1983 | Stein |
| 4,476,868 A | 10/1984 | Thompson et al. |
| 4,556,063 A | 12/1985 | Thompson et al. |
| 4,577,633 A | 3/1986 | Berkovits et al. |
| 4,587,970 A | 5/1986 | Holley et al. |
| 4,726,380 A | 2/1988 | Vollmann |
| 4,821,723 A | 4/1989 | Baker, Jr. et al. |
| 4,830,006 A | 5/1989 | Haluska |
| 4,880,005 A | 11/1989 | Pless et al. |
| 5,099,838 A | 3/1992 | Bordy |
| 5,117,824 A | 6/1992 | Keimel et al. |
| 5,131,388 A | 7/1992 | Pless et al. |
| 5,144,949 A | 9/1992 | Olson |
| 5,158,078 A | 10/1992 | Bennett et al. |
| 5,188,105 A | 2/1993 | Keimel |
| 5,269,298 A | 12/1993 | Adams et al. |
| 5,312,453 A | 5/1994 | Shelton et al. |
| 5,354,316 A | 10/1994 | Keimel |
| 5,545,186 A | 8/1996 | Olson |
| 5,601,615 A | 2/1997 | Markowitz |
| 5,683,426 A | 11/1997 | Greenhut et al. |
| 5,741,312 A | 4/1998 | Vonk et al. |
| 5,954,755 A | 9/1999 | Casavant |
| 5,960,686 A | 10/1999 | Bonow |
| 6,101,416 A * | 8/2000 | Sloman ........................ 607/28 |
| 6,345,201 B1 * | 2/2002 | Sloman et al. ................ 607/28 |
| 6,434,428 B1 * | 8/2002 | Sloman et al. ................ 607/28 |

OTHER PUBLICATIONS

"Onset and Stability for Ventricular Tachyarrhythmia Detection in an Implantable Pacer–Cardioverter–Defibrillator" Olson et al., Computers in Cardiology, Oct. 7–10, 1986, IEEE Computer Society Press, pp 167–170.

* cited by examiner

Primary Examiner—Kennedy Schaetzle

(57) ABSTRACT

A method and system for atrial capture detection based on far-field R-wave (FFRW) sensing is provided. After establishing that stable FFRW sensing exists, presence of atrial capture can be detected by atrial sensing of the FFRW in a predetermined FFRW detection window following an atrial pace. Threshold values for the atrial pace can be determined by varying an atrial test variable and observing whether a FFRW occurs in the FFRW detection window. In another embodiment, threshold values for the atrial pace can be determined by applying a search pace before the regular atrial pace, varying an atrial test variable for the search pace, and monitoring the movement of the FFRW between the FFRW detection window and a predetermined search detection window located before the FFRW detection window.

66 Claims, 9 Drawing Sheets

METHOD AND SYSTEM FOR ATRIAL CAPTURE DETECTION BASED ON FAR-FIELD R-WAVE SENSING

FIELD OF THE INVENTION

The present invention relates to the field of implanatable medical devices. More particularly, to cardiac pacing systems having atrial capture detection based on far-field R-wave sensing.

BACKGROUND OF THE INVENTION

Implantable cardiac pacing systems deliver a pacing pulse of sufficient amplitude and width to stimulate the heart. The pacing pulse must be above a threshold value before the heart tissue will respond. Although a pulse much greater than the threshold will evoke a response, a large energy pulse will deplete the implanted battery faster than a pulse just above the threshold. It is desirable to use a pacing pulse that is as small as safely required, one equal to the threshold times a safety factor. The threshold must be measured from time to time, because it changes with such factors as inflammation and fibrous tissue buildup near the electrode of the pacing system, medication, and the patient's general health. Currently, the threshold test must be performed at a hospital during a time-consuming, manual procedure.

Although much effort has been spent on developing threshold tests that automatically determine the threshold while the cardiac pacing system is in use, automatic atrial threshold tests are still a problem in modern pacemakers. The biggest problem is the measurement of the atrial evoked response, a small signal generated in the atrium immediately after an effective atrial stimulus. This signal is generated in response to the atrial stimulus and is caused by the depolarization of the atrial heart muscle cells. Normally, the atrial evoked response will be masked by the polarization signals. Polarization is a slowly decaying residual signal from the pace pulse and is normally a magnitude (10 to 100 times) bigger than the atrial evoked response, which has a range 0.5 to 5 mV.

There are two basic ways to minimize the polarization artifact. The first is the use of "low polarization" electrodes, electrodes that generate low polarization artifacts due to their construction and the use of specific electrode materials. The second is the use of a triphasic pulse, an output pulse consisting of three phases which can be optimized in such a way that there is no or a very low polarization artifact. The triphasic pulse typically uses two pulses of one polarity separated by a single pulse of the opposite polarity. Although detecting the atrial evoked response is the most direct way of discriminating between a captured and a non-captured output pulse, it is also the most difficult.

In patients with an intact AV conduction system and with electrodes in the atrium and the ventricle, there is another way of performing a threshold test. An effective pulse generated in the atrium will depolarize the atrium and will be passed on to the ventricles via the intact AV conduction system. A sensed ventricular signal (conducted R-wave) is in this case a confirmation of the effectiveness of the atrial stimulus. On the other hand, during a threshold test an ineffective atrial stimulus will not lead to a sensed ventricular R-wave in a specific window after the atrial stimulus. All these systems use the electrode in the ventricle to detect a ventricular depolarization (R-wave) caused initially by an atrial pulse and conducted via an intact AV conduction system. Therefore, these systems require a sensing electrode be installed and functioning in the ventricle.

U.S. Pat. No. 5,954,755 to Casavant discloses a pacing algorithm, and a device and system to implement it that facilitates the task of measuring atrial pacing thresholds and determining atrial capture. The algorithm checks for intact conduction, and in its presence, the measurement is executed in an ADI pacing mode. The test can be used if the patient has no evidence of heart block, enabling the monitoring of ventricular sensed events.

U.S. Pat. No. 5,601,615 to Markowitz et al. discloses a first atrial and ventricular threshold test regimen for use with patients having intact A-V conduction or first degree AV block, A-pace pulses are delivered at a test escape interval and A-V delay. Atrial loss of capture (ALOC) in response to an A-pace test stimulus is declared by the absence of a detected ventricular depolarization (V-event) in the latter portion of the paced A-V delay interval following the delivery of the A-pace test stimulus.

U.S. Pat. No. 5,683,426 to Greenhut et al. discloses an invention pertaining to an apparatus, such as a pacemaker, for detecting a far field R-wave in an atrial lead coupled to the pacemaker. The R-wave may be used for a number of different purposes, depending on the condition of the patient. First, the R-wave may be used to detect the occurrence and progression of AV nodal block in a patient. If AV nodal block is detected, its progression is monitored to determine when such a condition requires additional therapeutic steps. If the clinician confirms that AV nodal block is not present, the R-wave may be used to detect and confirm atrial capture.

Another threshold test system is the double pulse system disclosed in U.S. Pat. No. 5,741,312 to Vonk et al. There is disclosed a pacemaker system with capture verification and threshold testing, in which the pacemaker waits after each change in delivered pace pulses for a stabilization interval, in order to minimize polarization and enhance capture verification. The threshold test utilizes a pace pulse pair, comprising a prior search pulse which is varied during the test, and the regular pacing pulse which is above threshold. The evoked response is detected from the evoked P wave and evoked R wave for atrial capture and ventricle capture, respectively.

The most pertinent prior art patents known at the present time are shown in the following table:

TABLE 1

| Prior Art Patents. | | |
|---|---|---|
| U.S. Pat. No. | Date | Inventor(s) |
| 5,954,755 | Sep. 21, 1999 | Casavant |
| 5,741,312 | Apr. 21, 1998 | Vonk et al. |
| 5,683,426 | Nov. 04, 1997 | Greenhut et al. |
| 5,601,615 | Feb. 02, 1997 | Markowitz et al. |

All patents listed in Table 1 above are hereby incorporated by reference herein in their respective entireties. As those of ordinary skill in the art will appreciate readily upon reading the Summary of the Invention, the Detailed Description of the Preferred Embodiments and the Claims set forth below, many of the devices and methods disclosed in the patents of Table 1 may be modified advantageously by using the teachings of the present invention.

SUMMARY OF THE INVENTION

The present invention is therefore directed to providing a system and method for determining an atrial capture threshold. The system of the present invention overcomes the problems, disadvantages and limitations of the prior art described above, and provides a more efficient and accurate means of determining an atrial capture threshold.

The present invention has certain objects. That is, various embodiments of the present invention provide solutions to one or more problems existing in the prior art respecting the determination of an atrial capture threshold. Those problems include, without limitation: (a) difficulty in measuring the atrial evoked response because the atrial evoked response may be masked by polarization signals, (b) need to measure the atrial evoked response in close proximity to the atrial pacing pulse; (c) infrequent threshold testing, because the threshold test is a time-consuming, manual test that can only be performed in the hospital, (d) need for a ventricular lead using ventricular activity to sense atrial capture, (e) need for special low polarization electrodes to measure atrial evoked response without masking by polarization signals, and (f) need for triphasic test pulses to measure atrial evoked response without masking by polarization signals.

In comparison to known techniques for determining an atrial capture threshold, various embodiments of the present invention provide one or more of the following advantages: (a) the ability to perform frequent, automatic threshold tests; (b) the ability to detect atrial capture by atrial sensing when the polarization signal is relatively large; (c) the ability to detect atrial capture by atrial sensing using the Far Field R-Wave, rather than ventricular sensing; and (d) the ability to perform threshold testing while maintaining regular pacing to the patient.

Some of the embodiments of the present invention include one or more of the following features: (a) an IMD having an automatic threshold test that uses Far Field R-Wave detection to indicate atrial capture, (b) an IMD having an automatic threshold test that uses dual pulses and time shifting of the Far Field R-Wave to indicate atrial capture; (c) methods of performing threshold tests that use Far Field R-Wave detection to indicate atrial capture, (d) methods of performing threshold tests that use dual pulses and time shifting of the Far Field R-Wave to indicate atrial capture, and (e) methods of performing threshold tests that use atrial test pulses and atrial sensing.

At least some embodiments of the present invention involve determining that the patient has a stable Far Field R-Wave (FFRW) pattern that can be used to detect atrial capture, then measuring the FFRW detection time between an atrial pace and FFRW atrial sense. The FFRW detection time is used to determine a FFRW detection window. An atrial pace of a given amplitude and pulse width is applied and the resulting FFRW detected in the FFRW detection window. The atrial test variable, either amplitude or pulse width, is decreased and another atrial pace is applied. If atrial capture is indicated by a FFRW detected in the FFRW detection window, the atrial test variable is decreased and the cycle is repeated. When the atrial test variable has been decreased until no FFRW is detected, that amplitude or pulse width setting is the threshold value and the atrial threshold test ends.

Other embodiments of the present invention involve a double pulse atrial threshold testing method, applying a search pace and a regular pace. It is first determined that the patient has a stable Far Field R-Wave (FFRW) pattern that can be used to detect atrial capture. The FFRW detection time between an atrial pace and FFRW atrial sense is measured. The FFRW detection time is used to determine a regular FFRW detection window where the FFRW normally occurs and a search FFRW detection window before the regular FFRW detection window. The search FFRW detection window precedes the regular FFRW detection window by the time interval between the search pace and the regular pace. A search pace of zero or small amplitude and pulse width is applied and the regular atrial pace applied a time interval later. If no FFRW is detected in the search FFRW detection window, the atrial test variable of the search pace is increased. The atrial test variable can be either amplitude or pulse width, as desired. Another search pace and regular atrial pace are then applied. The cycle is repeated until a FFRW is detected in the search FFRW detection window, indicating atrial capture of the search pace. When the amplitude or pulse width setting of the search pace has been increased until a FFRW is detected in the search FFRW detection window, that amplitude or pulse width setting is the threshold value and the atrial threshold test ends.

BRIEF DESCRIPTION OF THE DRAWINGS

The above, and other objects, advantages and features of the present invention will be more readily understood from the following detailed description of the preferred embodiments thereof, when considered in conjunction with the drawings, in which like reference numerals indicate identical structures throughout the several views, and wherein.

DETAILED DESCRIPTION OF THE PRESENTLY PREFERRED EMBODIMENTS

Figure 1:
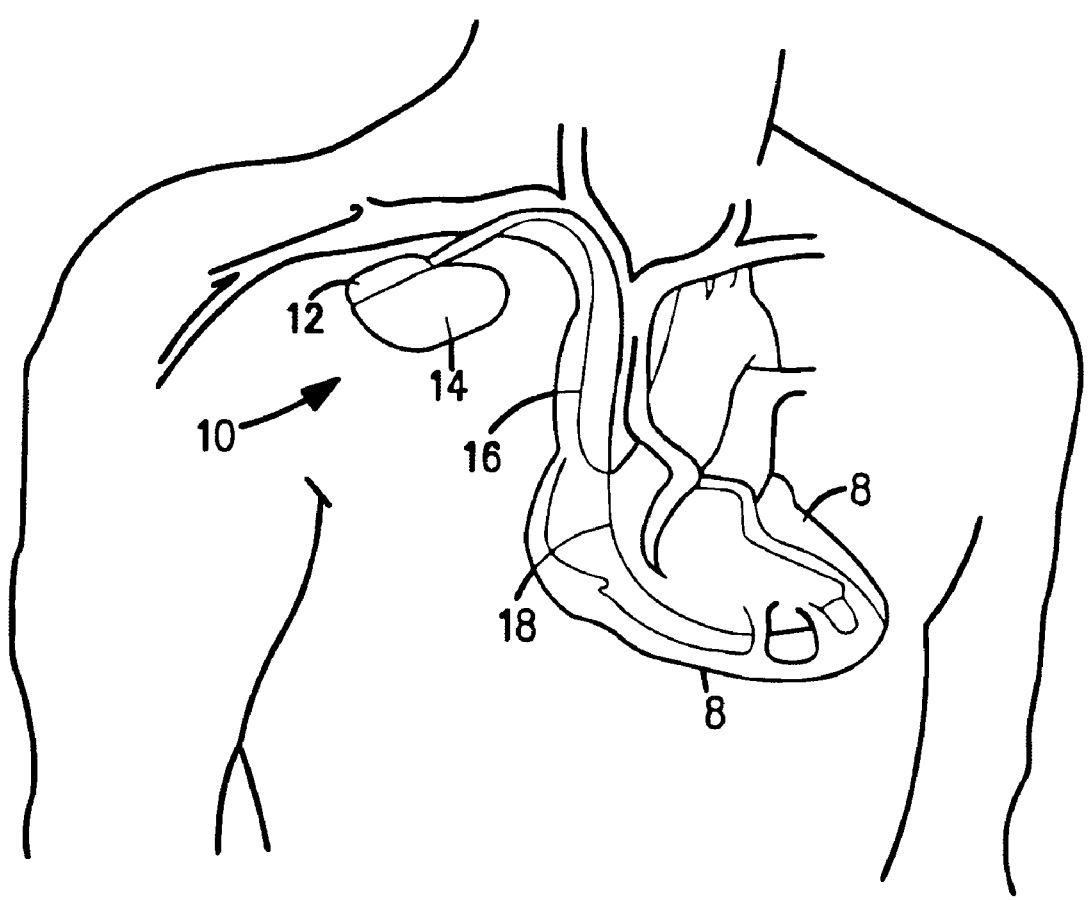
FIG. 1 is a schematic view of one embodiment of an implantable medical device in situ, made in accordance with the present invention.

FIG. 1 is a simplified schematic view of one embodiment of implantable medical device ("IMD") 10 of the present invention. IMD 10 shown in FIG. 1 is a pacemaker comprising at least one of pacing and sensing leads 16 and 18 attached to hermetically sealed enclosure 14 and implanted near human or mammalian heart 8. Pacing and sensing leads 16 and 18 sense electrical signals attendant to the depolarization and re-polarization of the heart 8, and further provide pacing pulses for causing depolarization of cardiac tissue in the vicinity of the distal ends thereof. Leads 16 and 18 may have unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al. or U.S. Pat. No. 5,144,949 to Olson, all hereby incorporated by reference herein, each in its respective entirety.

Figure 2:
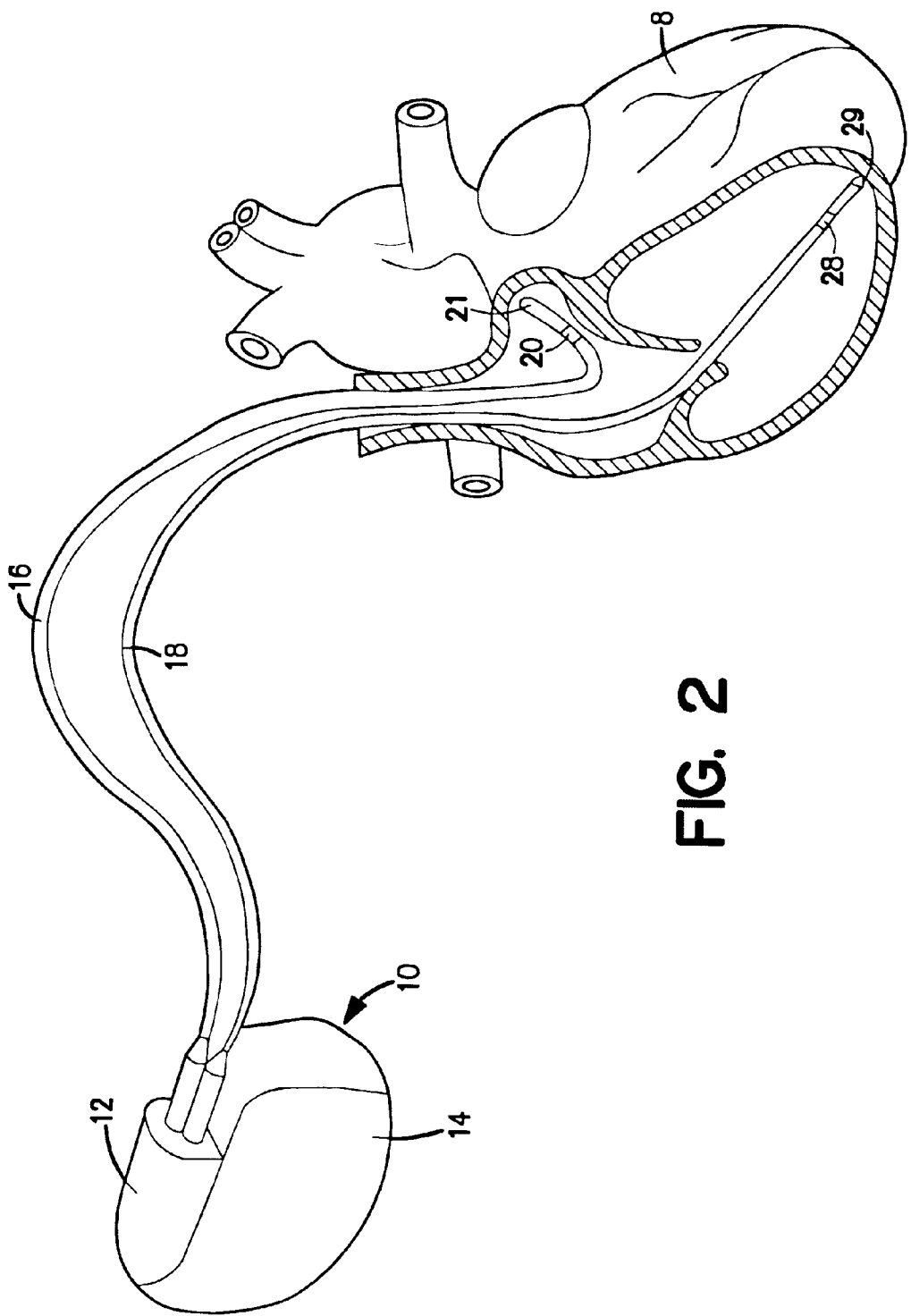
FIG. 2 is another schematic view of an embodiment of the implantable medical device of FIG. 1, made in accordance with the present invention.

FIG. 2 shows connector module 12 and hermetically sealed enclosure 14 of IMD 10 located in and near human or mammalian heart 8. Atrial and ventricular pacing leads 16 and 18 extend from connector header module 12 to the right atrium and ventricle, respectively, of heart 8. Atrial electrodes 20 and 21 disposed at the distal end of atrial pacing lead 16 are located in the right atrium. Ventricular electrodes 28 and 29 at the distal end of ventricular pacing lead 18 are located in the right ventricle.

Figure 3:
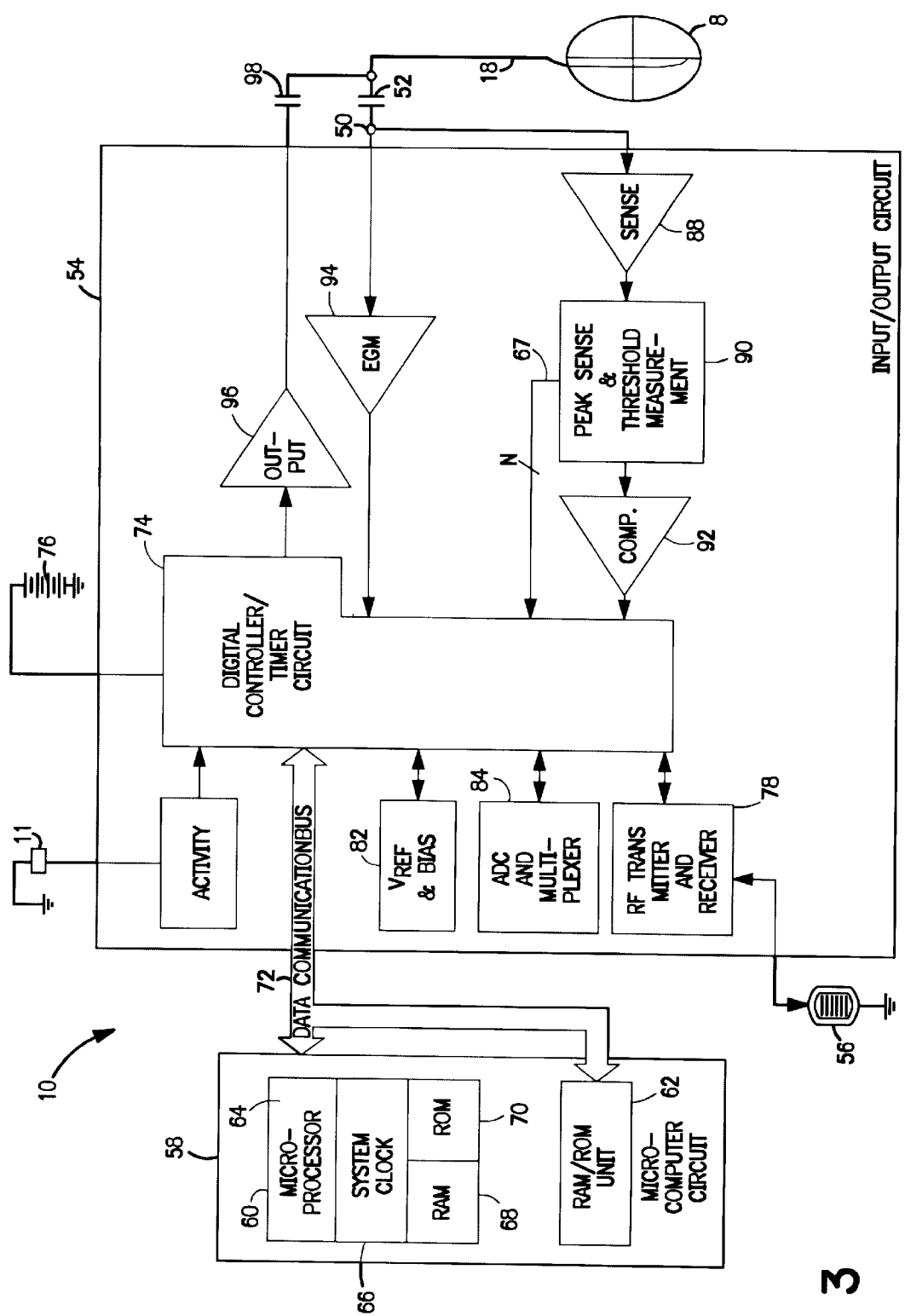
FIG. 3 is a block diagram illustrating components of an embodiment of the implantable medical device of FIG. 1, made in accordance with the present invention.

FIG. 3 shows a block diagram illustrating the constituent components of IMD 10 in accordance with one embodiment of the present invention, where IMD 10 is pacemaker having a microprocessor-based architecture. IMD 10 is shown as including activity sensor or accelerometer 11, which is preferably a piezoceramic accelerometer bonded to a hybrid circuit located inside enclosure 14. Activity sensor 11 typically (although not necessarily) provides a sensor output that varies as a function of a measured parameter relating to a patient's metabolic requirements. For the sake of convenience, IMD 10 in FIG. 3 is shown with lead 18 only connected thereto; similar circuitry and connections not explicitly shown in FIG. 3 apply to lead 16.

IMD 10 in FIG. 3 is most preferably programmable by means of an external programming unit (not shown in the Figures). One such programmer is the commercially available Medtronic Model 9790 programmer, which is microprocessor-based and provides a series of encoded signals to IMD 10, typically through a programming head which transmits or telemeters radio-frequency (RF) encoded signals to IMD 10. Such a telemetry system is described in U.S. Pat. No. 5,312,453 to Wyborny et al., hereby incorporated by reference herein in its entirety. The programming methodology disclosed in Wyborny et al.'s '453 patent is identified herein for illustrative purposes only. Any of a number of suitable programming and telemetry methodologies known in the art may be employed so long as the desired information is transmitted to and from the pacemaker.

As shown in FIG. 3, lead 18 is coupled to node 50 in IMD 10 through input capacitor 52. Activity sensor or accelerometer 11 is most preferably attached to a hybrid circuit located inside hermetically sealed enclosure 14 of IMD 10. The output signal provided by activity sensor 11 is coupled to input/output circuit 54. Input/output circuit 54 contains analog circuits for interfacing to heart 8, activity sensor 11, antenna 56 and circuits for the application of stimulating pulses to heart 8. The rate of heart 8 is controlled by software-implemented algorithms stored microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al., hereby incorporated by reference herein in its entirety. On-board circuit 60 preferably includes microprocessor 64, system clock circuit 66 and on-board RAM 68 and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of IMD 10 is not shown in the Figures. Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063 issued to Thompson et al., hereby incorporated by reference herein in its entirety, or to that disclosed in the above-referenced '453 patent to Wyborny et al. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 3, $V_{REF}$ and Bias circuit 82 most preferably generates stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are coupled by data bus 72 to digital controller/timer circuit 74, where digital timers and counters establish the overall escape interval of the IMD 10 as well as various refractory, blanking and other timing windows for controlling the operation of peripheral components disposed within input/output circuit 54.

Digital controller/timer circuit 74 is preferably coupled to sensing circuitry, including sense amplifier 88, peak sense and threshold measurement unit 90 and comparator/threshold detector 92. Circuit 74 is further preferably coupled to electrogram (EGM) amplifier 94 for receiving amplified and processed signals sensed by lead 18. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is then provided to comparator/threshold detector 92. By way of example, sense amplifier 88 may correspond to that disclosed in U.S. Pat. No. 4,379,459 to Stein, hereby incorporated by reference herein in its entirety.

The electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al., hereby incorporated by reference herein in its entirety. Output pulse generator 96 provides pacing stimuli to patient's heart 8 through coupling capacitor 98 in response to a pacing trigger signal provided by digital controller/timer circuit 74 each time the escape interval times out, an externally transmitted pacing command is received or in response to other stored commands as is well known in the pacing art. By way of example, output amplifier 96 may correspond generally to an output amplifier disclosed in U.S. Pat. No. 4,476,868 to Thompson, hereby incorporated by reference herein in its entirety.

The specific embodiments of input amplifier 88, output amplifier 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 8.

In some preferred embodiments of the present invention, IMD 10 may operate in various non-rate-responsive modes, including, but not limited to, DDD, DDI, VVI, VOO and VVT modes. In other preferred embodiments of the present invention, IMD 10 may operate in various rate-responsive, including, but not limited to, DDDR, DDIR, VVIR, VOOR and VVTR modes. Some embodiments of the present invention are capable of operating in both non-rate-responsive and rate responsive modes. Moreover, in various embodiments of the present invention IMD 10 may be programmably configured to operate so that it varies the rate at which it delivers stimulating pulses to heart 8 only in response to one or more selected sensor outputs being generated. Numerous pacemaker features and functions not explicitly mentioned herein may be incorporated into IMD 10 while remaining within the scope of the present invention.

The present invention is not limited in scope to single-sensor or dual-sensor pacemakers, and is not limited to IMD's comprising activity or pressure sensors only. Nor is the present invention limited in scope to single-chamber pacemakers, single-chamber leads for pacemakers or single-sensor or dual-sensor leads for pacemakers. Thus, various embodiments of the present invention may be practiced in conjunction with more than two leads or with multiple-chamber pacemakers, for example. At least some embodiments of the present invention may be applied equally well in the contexts of single-, dual-, triple- or quadruple-chamber pacemakers or other types of IMD's. See, for example, U.S. Pat. No. 5,800,465 to Thompson et al., hereby incorporated by reference herein in its entirety, as are all U.S. Patents referenced therein.

IMD 10 may also be a pacemaker-cardioverter-defibrillator ("PCD") corresponding to any of numerous commercially available implantable PCD's. Various embodiments of the present invention may be practiced in conjunction with PCD's such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless and U.S. Pat. No. 4,821,723 to Baker et al., all hereby incorporated by reference herein, each in its respective entirety.

Figure 4:
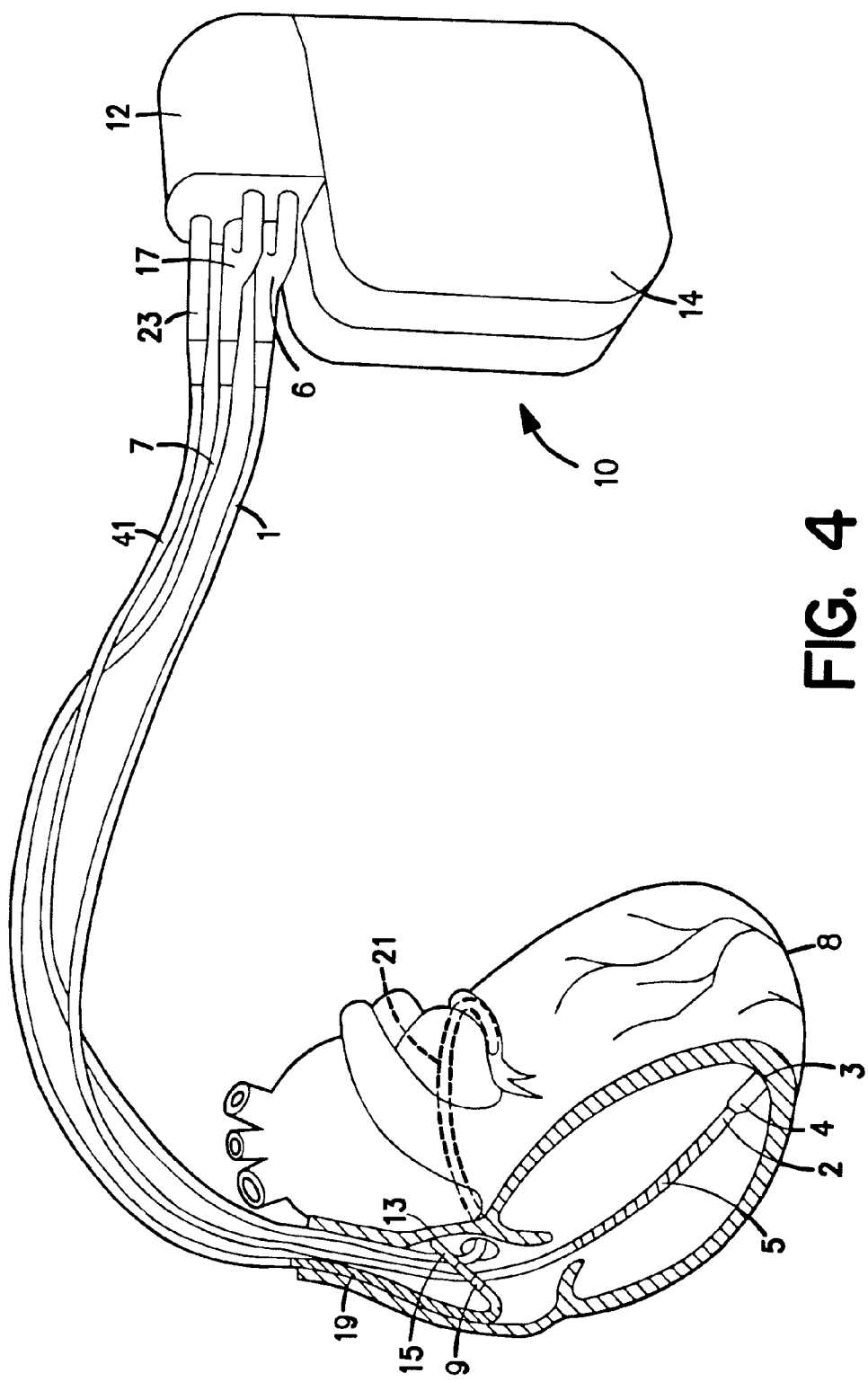
FIG. 4 is a schematic view of another embodiment of an implantable medical device, made in accordance with the present invention.
Figure 5:
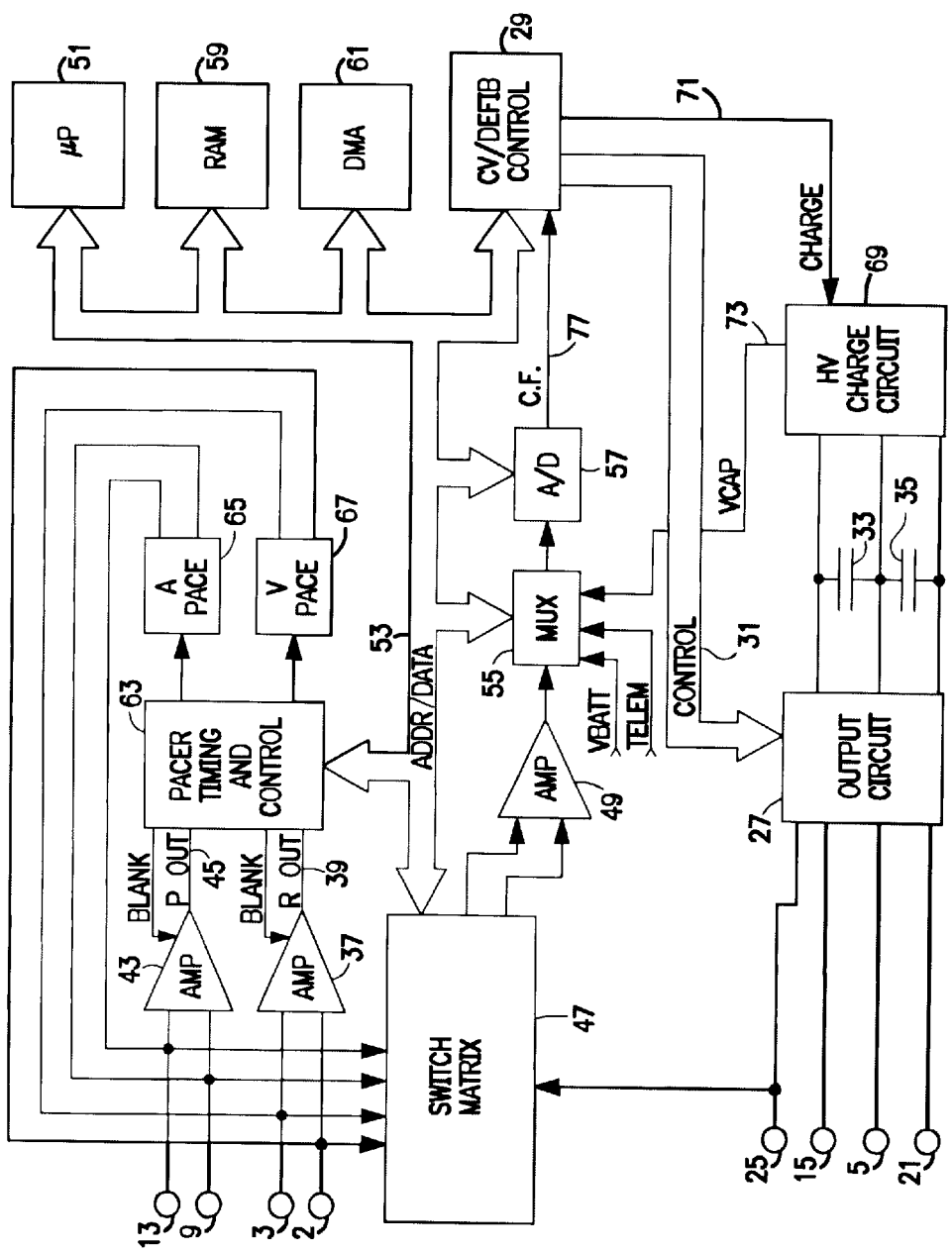
FIG. 5 is a block diagram illustrating components of an embodiment of the implantable medical device of FIG. 4, made in accordance with the present invention.

FIGS. 4 and 5 illustrate one embodiment of IMD 10 and a corresponding lead set of the present invention, where IMD 10 is a PCD. In FIG. 4, the ventricular lead takes the form of leads disclosed in U.S. Pat. Nos. 5,099,838 and 5,314,430 to Bardy, and includes an elongated insulative lead body 1 carrying three concentric coiled conductors separated from one another by tubular insulative sheaths. Located adjacent the distal end of lead 1 are ring electrode 2, extendable helix electrode 3 mounted retractably within insulative electrode head 4 and elongated coil electrode 5. Each of the electrodes is coupled to one of the coiled conductors within lead body 1. Electrodes 2 and 3 are employed for cardiac pacing and for sensing ventricular depolarizations. At the proximal end of the lead is bifurcated connector 6 which carries three electrical connectors, each coupled to one of the coiled conductors. Defibrillation electrode 5 may be fabricated from platinum, platinum alloy or other materials known to be usable in implantable defibrillation electrodes and may be about 5 cm in length.

The atrial/SVC lead shown in FIG. 4 includes elongated insulative lead body 7 carrying three concentric coiled conductors separated from one another by tubular insulative sheaths corresponding to the structure of the ventricular lead. Located adjacent the J-shaped distal end of the lead are ring electrode 9 and extendable helix electrode 13 mounted retractably within an insulative electrode head 15. Each of the electrodes is coupled to one of the coiled conductors within lead body 7. Electrodes 13 and 9 are employed for atrial pacing and for sensing atrial depolarizations. Elongated coil electrode 19 is provided proximal to electrode 9 and coupled to the third conductor within lead body 7. Electrode 19 preferably is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 17 carrying three electrical connectors, each coupled to one of the coiled conductors.

The coronary sinus lead shown in FIG. 4 assumes the form of a coronary sinus lead disclosed in the above cited '838 patent issued to Bardy, and includes elongated insulative lead body 41 carrying one coiled conductor coupled to an elongated coiled defibrillation electrode 21. Electrode 21, illustrated in broken outline in FIG. 4, is located within the coronary sinus and great vein of the heart. At the proximal end of the lead is connector plug 23 carrying an electrical connector coupled to the coiled conductor. The coronary sinus/great vein electrode 21 may be about 5 cm in length.

Implantable PCD 10 is shown in FIG. 4 in combination with leads 1, 7 and 41, and lead connector assemblies 23, 17 and 6 inserted into connector block 12. Optionally, insulation of the outward facing portion of housing 14 of PCD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other that those shown in FIG. 4 may be practiced in conjunction with the present invention, such as those shown in U.S. Pat. No. 5,690,686 to Min et al., hereby incorporated by reference herein in its entirety.

FIG. 5 is a functional schematic diagram of one embodiment of implantable PCD 10 of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

IMD 10 is provided with an electrode system. If the electrode configuration of FIG. 4 is employed, the correspondence to the illustrated electrodes is as follows. Electrode 25 in FIG. 5 includes the uninsulated portion of the housing of PCD 10. Electrodes 25, 15, 21 and 5 are coupled to high voltage output circuit 27, which includes high voltage switches controlled by CV/defib control logic 29 via control bus 31. Switches disposed within circuit 27 determine which electrodes are employed and which electrodes are coupled to the positive and negative terminals of the capacitor bank (which includes capacitors 33 and 35) during delivery of defibrillation pulses.

Electrodes 2 and 3 are located on or in the ventricle and are coupled to the R-wave amplifier 37, which preferably takes the form of an automatic gain controlled amplifier providing an adjustable sensing threshold as a function of the measured R-wave amplitude. A signal is generated on R-out line 39 whenever the signal sensed between electrodes 2 and 3 exceeds the present sensing threshold.

Electrodes 9 and 13 are located on or in the atrium and are coupled to the P-wave amplifier 43, which preferably also takes the form of an automatic gain controlled amplifier providing an adjustable sensing threshold as a function of the measured P-wave amplitude. A signal is generated on P-out line 45 whenever the signal sensed between electrodes 9 and 13 exceeds the present sensing threshold. The general operation of R-wave and P-wave amplifiers 37 and 43 may correspond to that disclosed in U.S. Pat. No. 5,117,824, by Keimel et al., issued Jun. 2, 1992, for "An Apparatus for Monitoring Electrical Physiologic Signals", hereby incorporated by reference herein in its entirety.

Switch matrix 47 is used to select which of the available electrodes are coupled to wide band (0.5–200 Hz) amplifier 49 for use in digital signal analysis. Selection of electrodes is controlled by the microprocessor 51 via data/address bus 53, which selections may be varied as desired. Signals from the electrodes selected for coupling to bandpass amplifier 49 are provided to multiplexer 55, and thereafter converted to multi-bit digital signals by A/D converter 57, for storage in random access memory 59 under control of direct memory access circuit 61. Microprocessor 51 may employ digital signal analysis techniques to characterize the digitized signals stored in random access memory 59 to recognize and classify the patient's heart rhythm employing any of the numerous signal processing methodologies known to the art.

The remainder of the circuitry is dedicated to the provision of cardiac pacing, cardioversion and defibrillation therapies, and, for purposes of the present invention may correspond to circuitry known to those skilled in the art. The following exemplary apparatus is disclosed for accomplishing pacing, cardioversion and defibrillation functions. Pacer timing/control circuitry 63 preferably includes programmable digital counters which control the basic time intervals associated with DDD, VVI, DVI, VDD, AAI, DDI and other modes of single and dual chamber pacing well known to the art. Circuitry 63 also preferably controls escape intervals associated with anti-tachyarrhythmia pacing in both the atrium and the ventricle, employing any anti-tachyarrhythmia pacing therapies known to the art.

Intervals defined by pacing circuitry 63 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 51, in response to stored data in memory 59 and are communicated to pacing circuitry 63 via address/data bus 53. Pacer circuitry 63 also determines the amplitude of the cardiac pacing pulses under control of microprocessor 51.

During pacing, escape interval counters within pacer timing/control circuitry 63 are reset upon sensing of R-waves and P-waves as indicated by a signals on lines 39 and 45, and in accordance with the selected mode of pacing on time-out trigger generation of pacing pulses by pacer output circuitry 65 and 67, which are coupled to electrodes 9, 13, 2 and 3. Escape interval counters are also reset on generation of pacing pulses and thereby control the basic timing of cardiac pacing functions, including anti-tachyarrhythmia pacing. The durations of the intervals defined by escape interval timers are determined by microprocessor 51 via data/address bus 53. The value of the count present in the escape interval counters when reset by sensed R-waves and P-waves may be used to measure the durations of R-R intervals, P-P intervals, P-R intervals and R-P intervals, which measurements are stored in memory 59 and used to detect the presence of tachyarrhythmias.

Microprocessor 51 most preferably operates as an interrupt driven device, and is responsive to interrupts from pacer timing/control circuitry 63 corresponding to the occurrence sensed P-waves and R-waves and corresponding to the generation of cardiac pacing pulses. Those interrupts are provided via data/address bus 53. Any necessary mathematical calculations to be performed by microprocessor 51 and any updating of the values or intervals controlled by pacer timing/control circuitry 63 take place following such interrupts.

Detection of atrial or ventricular tachyarrhythmias, as employed in the present invention, may correspond to tachyarrhythmia detection algorithms known in the art. For example, the presence of an atrial or ventricular tachyarrhythmia may be confirmed by detecting a sustained series of short R-R or P-P intervals of an average rate indicative of tachyarrhythmia or an unbroken series of short R-R or P-P intervals. The suddenness of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann, U.S. Pat. No. 4,880,005 issued to Pless et al. and U.S. Pat. No. 4,830,006 issued to Haluska et al., all incorporated by reference herein, each in its respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, IEEE Computer Society Press, pp. 167–170, also incorporated by reference herein in its entirety. Atrial fibrillation detection methodologies are disclosed in Published PCT application Ser. No. US92/02829, Publication No. WO92/18198, by Adams et al., and in the article "Automatic Tachycardia Recognition", by Arzbaecher et al., published in PACE, May–June, 1984, pp. 541–547, both of which are incorporated by reference herein in their entireties.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 51 into the pacer timing and control circuitry 63, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 4,726,380, issued to Vollmann et al. on Feb. 23, 1988 and U.S. Pat. No. 4,587,970, issued to Holley et al. on May 13, 1986, all of which are incorporated herein by reference in their entireties, may also be employed.

In the event that generation of a cardioversion or defibrillation pulse is required, microprocessor 51 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 51 activates cardioversion/defibrillation control circuitry 29, which initiates charging of the high voltage capacitors 33 and 35 via charging circuit 69, under the control of high voltage charging control line 71. The voltage on the high voltage capacitors is monitored via VCAP line 73, which is passed through multiplexer 55 and in response to reaching a predetermined value set by microprocessor 51, results in generation of a logic signal on Cap Full (CF) line 77 to terminate charging. Thereafter, timing of the delivery of the defibrillation or cardioversion pulse is controlled by pacer timing/control circuitry 63. Following delivery of the fibrillation or tachycardia therapy microprocessor 51 returns the device to a cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al. and U.S. Pat. No. 4,316,472 to Mirowski et al., hereby incorporated by reference herein, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., all hereby incorporated by reference herein in their entireties, may also be employed.

Continuing to refer to FIG. 5, delivery of cardioversion or defibrillation pulses is accomplished by output circuit 27 under the control of control circuitry 29 via control bus 31. Output circuit 27 determines whether a monophasic or biphasic pulse is delivered, the polarity of the electrodes and which electrodes are involved in delivery of the pulse. Output circuit 27 also includes high voltage switches which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in the above cited patent issued to Mehra and in U.S. Pat. No. 4,727,877, hereby incorporated by reference herein in its entirety.

An example of circuitry which may be used to control delivery of monophasic pulses is disclosed in U.S. Pat. No. 5,163,427 to Keimel, also incorporated by reference herein in its entirety. Output control circuitry similar to that disclosed in U.S. Pat. No. 4,953,551 to Mehra et al. or U.S. Pat. No. 4,800,883 to Winstrom, both incorporated by reference herein in their entireties, may also be used in conjunction with various embodiments of the present invention to deliver biphasic pulses.

Alternatively, IMD 10 may be an implantable nerve stimulator or muscle stimulator such as that disclosed in U.S. Pat. No. 5,199,428 to Obel et al., U.S. Pat. No. 5,207,218 to Carpentier et al. or U.S. Pat. No. 5,330,507 to Schwartz, or an implantable monitoring device such as that disclosed in U.S. Pat. No. 5,331,966 issued to Bennet et al., all of which are hereby incorporated by reference herein, each in its respective entirety. The present invention is believed to find wide application to any form of implantable electrical device for use in conjunction with electrical leads.

Figure 6:
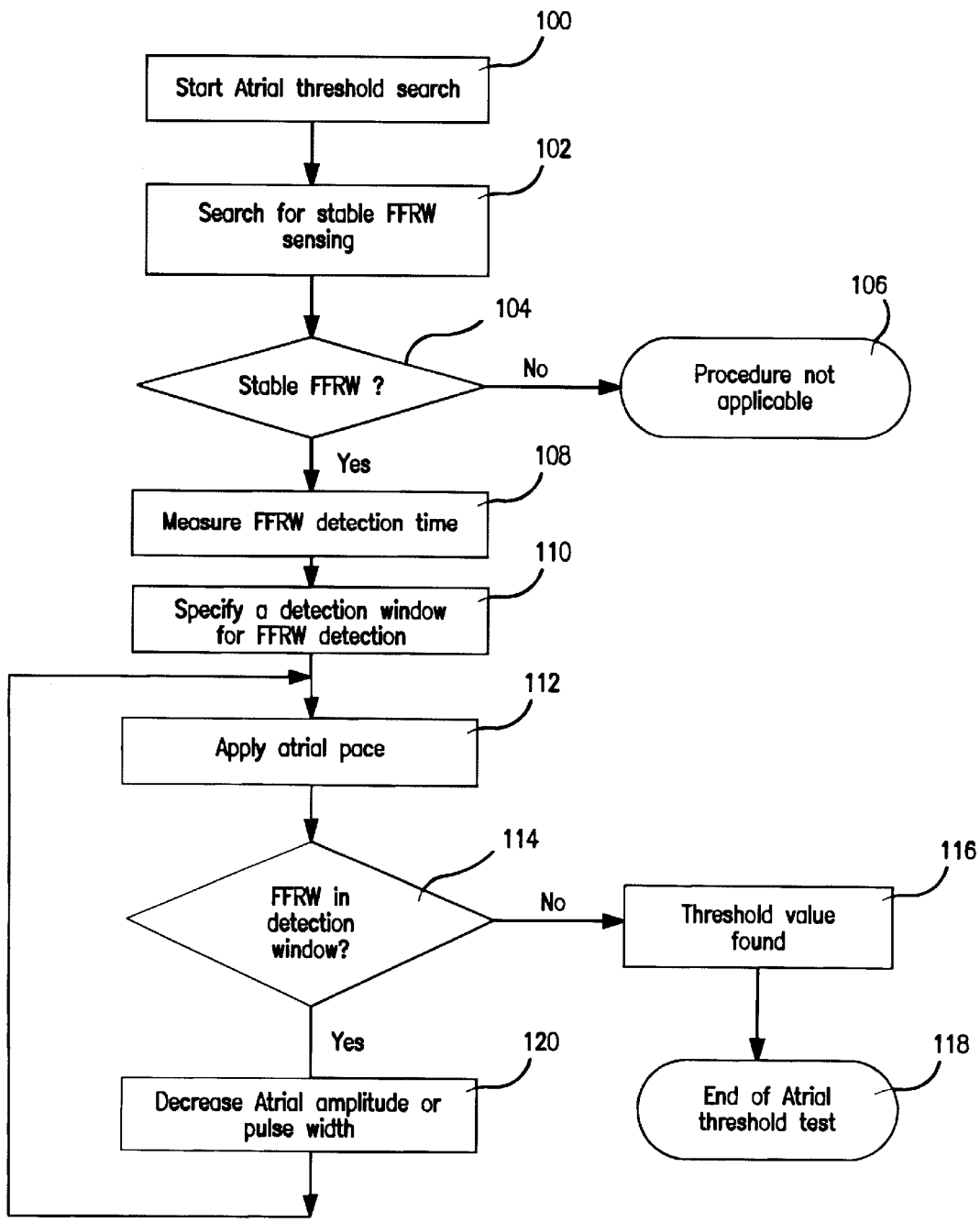
FIG. 6 is a flow chart of a method for determining an atrial capture threshold, in accordance with the present invention.

FIG. 6 shows a flow chart of a method for determining an atrial capture threshold in accordance with the present invention. An IMD 10 disposed within mammalian heart 8 is programmed to perform a threshold test and determine the minimum atrial pacing pulse that will produce atrial capture. The invention uses the Far Field R-wave (FFRW) to detect atrial capture.

The Far Field R-wave (FFRW) is a product of ventricular depolarization sensed in the atrium by the atrial electrode. The FFRW is normally an unwanted signal and is blanked by the input amplifiers of a pacemaker system so that it is not detected. The FFRW can be smaller or larger than intrinsic P-waves, so a separate sensitivity or detection system keyed to the amplitude of the FFRW signals can be used to detect the FFRW signals and ignore the intrinsic P-waves. No special input amplifiers are needed to sense the FFRW signal.

Form parameter analysis based on digital signal processing can also be used to discriminating intrinsic P-waves from FFRW signals. Specific form characteristics of the different signals are used to discriminate between the different signals. The FFRW signals normally have the highest amplitudes in the unipolar sensing mode.

The atrial threshold test starts at block 100 of FIG. 6. The atrial threshold test can be automatically performed by the IMD 10 or performed at an external request, such as by a physician performing the test. At block 102 the performance of the heart 8 is reviewed to verify that the response is suitable for threshold testing using the FFRW to indicate atrial capture. This threshold testing technique requires that the heart 8 have an intact AV conduction system, that is, that the heart 8 is able to transmit the signal from the atrial pace to the ventricle to produce a ventricular pulse, and the ventricle is able to return a FFRW to the atrium. A stable FFRW sensing is determined by pacing the heart 8 at a normal pulse rate and verifying that a FFRW is consistently sensed at the atrium. Depending on the patient, 5 to 20 sequential paces are sufficient to establish whether or not stable FFRW sensing is present and, typically, 10 sequential paces can be used.

Block 104 is the decision point for deciding whether to proceed with the atrial threshold test. If stable FFRW sensing was not found in the procedure of block 102, the atrial threshold test cannot be used and the procedure terminates at block 106. If stable FFRW sensing was found in the procedure of block 102, the atrial threshold test can be used and the procedure proceeds to block 108.

The FFRW detection time, defined as the interval from applying the atrial pace until sensing the FFRW, is determined in block 108. The FFRW detection time can be determined from the data obtained in the block 102 step of verifying that the response is suitable for threshold testing or can be obtained by performing a new series of atrial pace to FFRW sense measurements. Although the FFRW detection time will vary greatly between patients and is affected by external factors such as medication, the FFRW detection time is typically in the range of 80 to 220 msec. Although the FFRW detection time is different for each patient and can vary over a wide range (80 to 220 ms), it is relatively fixed during the short time period of a single threshold test.

At block 110, an FFRW detection window is established. The FFRW detection window is the time period following an atrial pace in which detection of a FFRW indicates atrial capture of the atrial pace. The detection window is centered on the mean value of the FFRW detection time, calculated using data from the stable FFRW sensing procedure of block 102. A typical FFRW detection window would be 50 msec. long and centered on the mean value of the FFRW detection time, that is, the mean value of the FFRW detection time plus (+) 25 ms and minus (−) 25 ms.

An atrial pace of a given amplitude and pulse width is then applied at block 112. The initial pace parameters are selected to assure that atrial capture will occur and a FFRW will be detected in the FFRW detection window, and can be determined from either the data obtained in the block 102 step of verifying that the response is suitable for threshold testing or the data obtained in the block 108 step of determining the FFRW detection time.

Block 114 is the decision point for deciding whether the applied atrial pace was above the threshold value so that a FFRW is detected in the FFRW detection window. If a FFRW is detected in the FFRW detection window indicating the applied atrial pace was above the threshold value, the process continues to the iterative path through block 120. If no FFRW is detected in the FFRW detection window indicating the applied atrial pace was below the threshold value, the process continues to the end path through block 116.

The iterative path through block 120 decreases the atrial test variable for the next applied atrial pace. The atrial test variable is changed in small steps to approach the threshold gradually and so as not to overshoot. The atrial test variable can be either the atrial pace amplitude or pulse width. Atrial pace amplitude can be changed by 0.1 to 0.5 V steps and is typically changed by a 0.1 V step. The value of change depends on the atrial pace amplitude. If the amplitude is large, the step value would be large too. For example, a 0.5V step used for a 5V atrial pace amplitude. If the atrial pace amplitude is small or close to the threshold, the step value will be small, e.g., 0.1 V. The pulse width typically would be changed by 0.05 msec per step. In an alternate embodiment, several iterations could be performed before the value of the atrial test variable is changed to assure that the atrial test variable has not reached the threshold.

The steps of block 112, block 114, and block 120 repeat until no FFRW is detected in the FFRW window at block 114. When no FFRW is detected in the FFRW detection window, the threshold value of the atrial test variable has been found (block 116) and the atrial threshold test ends (block 118).

Figure 7A:
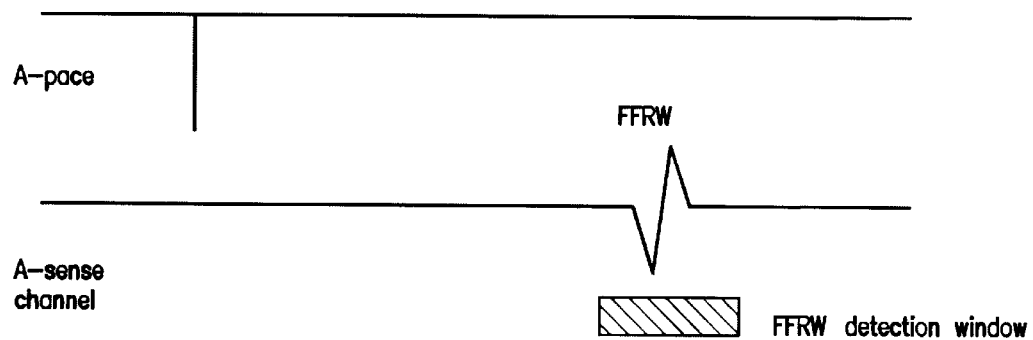
FIGS. 7A & 7B are timing diagrams of a method for determining an atrial capture threshold, in accordance with the present invention.
Figure 7B:
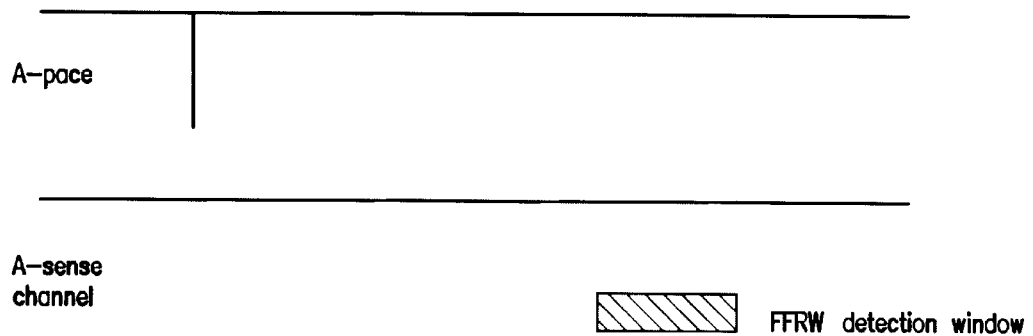

FIGS. 7A & 7B show timing diagrams of a method for determining an atrial capture threshold in accordance with the present invention. FIG. 7A shows the case where the atrial pace above the threshold value and FIG. 7B shows the case where the atrial pace is below the threshold value. In FIG. 7A, the upper line labeled A-pace shows application of an atrial pace with an amplitude above the threshold value. The lower line labeled A-sense channel shows sensing the FFRW within the FFRW detection window. The FFRW returned from the ventricle indicates that the atrial pace was above the threshold value and resulted in atrial capture. In FIG. 7B, the upper line labeled A-pace shows application of an atrial pace with an amplitude at or below the threshold value. The lower line labeled A-sense channel shows the absence of the FFRW from the FFRW detection window. No FFRW returned from the ventricle, so the atrial pace was at or below the threshold value for atrial capture.

Figure 8:
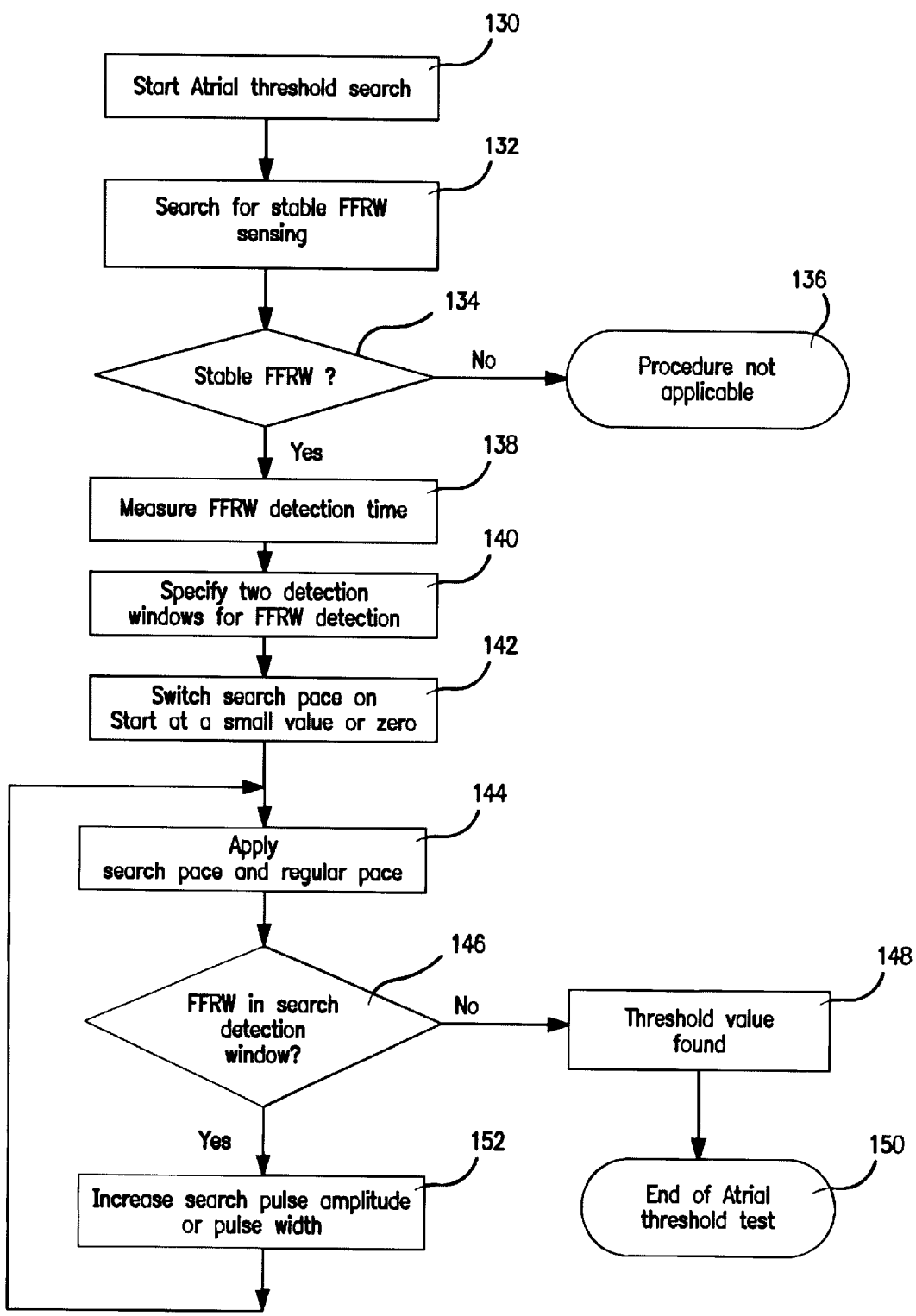
FIG. 8 is a flow chart of a dual pulse method for determining an atrial capture threshold, in accordance with the present invention.

FIG. 8 shows a flow chart of a dual pulse method for determining an atrial capture threshold in accordance with the present invention. An IMD 10 disposed within mammalian heart 8 is programmed to perform a threshold test and determine the minimum atrial pacing pulse that will produce atrial capture.

The dual pulse method for determining an atrial capture threshold uses a regular pace and a search pace applied in the atrium. The regular pulse is large enough to ensure atrial capture in all cases. The search pace is applied a short time before the regular pace, typically 50 to 100 msec. The advantage of the dual pulse method is that there is effective stimulation of the heart throughout the threshold test, either by the regular pace or by the search pace. If there is atrial capture on the search pace, the regular pace will be ineffective because the heart muscle cells are in the refractory period. If the search pulse is below threshold, the regular pace makes sure that regular heart rhythm is maintained. The threshold value is determined by looking for a time shift in the FFRW corresponding to the time difference between the search pace and the regular pace.

The atrial threshold test starts at block 130 of FIG. 8. The atrial threshold test can be automatically performed by the IMD 10 or performed at an external request, such as by a physician performing the test. At block 132, the performance of the heart 8 is reviewed to verify that the response is suitable for threshold testing using the FFRW to indicate atrial capture. This threshold testing technique requires that the heart 8 have an intact AV conduction system, that is, that the heart 8 is able to transmit the signal from the atrial pace to the ventricle to produce a ventricular pulse, and the ventricle is able to return a FFRW to the atrium. A stable FFRW sensing is determined by pacing the heart 8 at a normal pulse rate and verifying that a FFRW is consistently sensed at the atrium. Depending on the patient, 5 to 20 sequential paces are sufficient to establish whether or not stable FFRW sensing is present and, typically, 10 sequential paces can be used.

Block 134 is the decision point for deciding whether to proceed with the atrial threshold test. If stable FFRW sensing was not found in the procedure of block 132, the atrial threshold test cannot be used and the procedure terminates at block 136. If stable FFRW sensing was found in the procedure of block 132, the atrial threshold test can be used and the procedure proceeds to block 138.

The FFRW detection time, defined as the interval from applying the atrial pace until sensing the FFRW, is determined in block 138. The FFRW detection time can be determined from the data obtained in the block 132 step of verifying that the response is suitable for threshold testing or can be obtained by performing a new series of atrial pace to FFRW sense measurements. Although the FFRW detection time will vary greatly between patients and is affected by external factors such as medication, the FFRW detection time is typically in the range of 80 to 220 msec. Although the FFRW detection time is different for each patient and can vary over a wide range (80 to 220 ms), it is relatively fixed during the short time period of a single threshold test.

At block 140, the search FFRW detection window and regular FFRW detection windows are established. The FFRW detection window is the time period following an atrial pace in which detection of a FFRW indicates atrial capture of the atrial pace. The detection window is centered on the mean value of the FFRW detection time, calculated using data from the stable FFRW sensing procedure of block 132. A typical FFRW detection window would be 50 msec. long and centered on the mean value of the FFRW detection time, that is, the mean value of the FFRW detection time plus (+) 25 ms and minus (−) 25 ms.

The search FFRW detection window is typically the same length as the regular FFRW detection window, but the start of the search FFRW detection window precedes the start of the regular FFRW detection window by the time difference between the search pace and the regular pace.

The search pace is turned on with the atrial test variable set to zero or to a minimum value well below the threshold value at block 142. The atrial test variable can be either the atrial pace amplitude or pulse width. The initial pace parameters are selected to assure that atrial capture will occur on the regular pace and will not occur on the search pace. The FFRW will be detected in the regular FFRW detection window because the regular pace will be the captured pace.

The search pace followed by the regular pace are then applied at block 144. The time difference between the search pace and the regular pace can be set to a specific value for a specific patient but is typically 50 msec and can vary from 25 msec to 125 msec. Block 146 is the decision point for deciding whether the applied search pace was above the threshold value so that a FFRW is detected in the search FFRW detection window. If a FFRW is detected in the search FFRW detection window indicating the applied search pace was above the threshold value, the process continues to the iterative path through block 152. If no FFRW is detected in the search FFRW detection window indicating the applied search pace was below the threshold value, the process continues to the end path through block 148.

The iterative path through block 152 increases the atrial test variable for the next applied search pace. The atrial test variable is changed in small steps to approach the threshold gradually and so as not to overshoot. The atrial test variable can be either the atrial pace amplitude or pulse width. Atrial pace amplitude can be changed by 0.1 to 0.5 V steps and is typically changed by a 0.1 V step. The value of change depends on the atrial pace amplitude. If the amplitude is large, the step value would be large too. For example, a 0.5V step used for a 5V atrial pace amplitude. If the atrial pace amplitude is small or close to the threshold, the step value will be small, e.g., 0.1V. The pulse width typically would be changed by 0.05 msec per step. In an alternate embodiment, several iterations could be performed before the value of the atrial test variable is changed to assure that the atrial test variable has not reached the threshold.

The steps of block 144, block 146, and block 152 repeat until the FFRW is detected in the search FFRW detection window at block 146. When the FFRW is detected in the search FFRW detection window, the threshold value of the atrial test variable has been found (block 148) and the atrial threshold test ends (block 150).

Figure 9A:
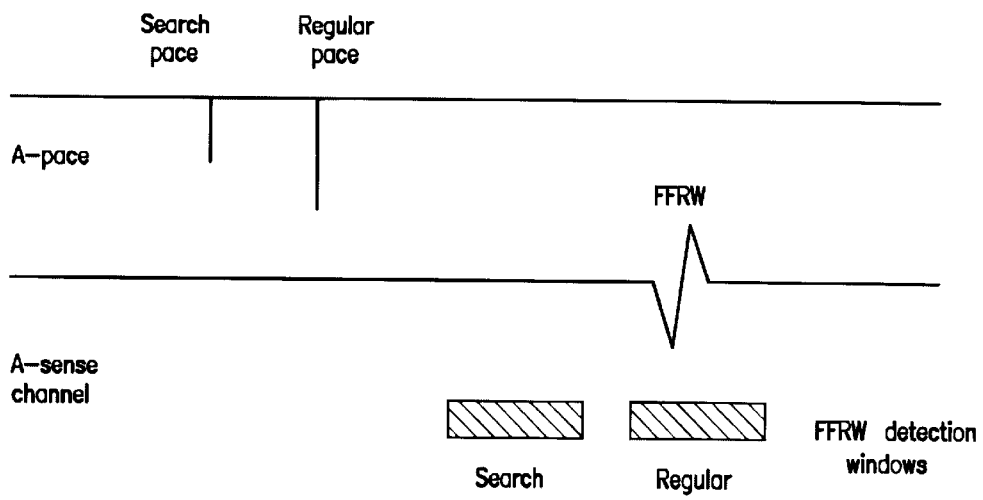
FIGS. 9A & 9B are timing diagrams of a dual pulse method for determining an atrial capture threshold, in accordance with the present invention.
Figure 9B:
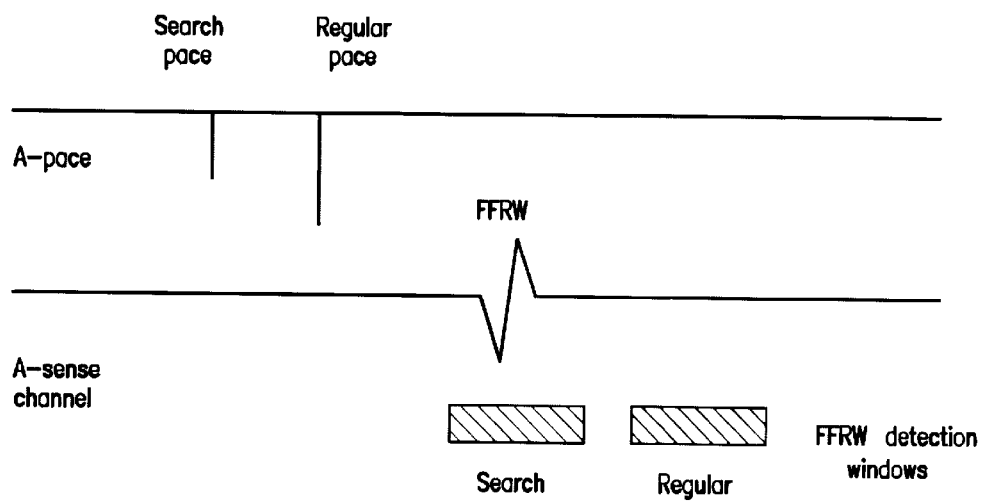

FIGS. 9A & 9B show timing diagrams of a dual pulse method for determining an atrial capture threshold in accordance with the present invention. FIG. 9A shows the case where the search pace is below the threshold value and the regular pace is captured. FIG. 9B shows the case where the atrial pace is above the threshold value and the search pace is captured.

In FIG. 9A, the upper line labeled A-pace shows application of an search pace with an amplitude below the threshold value and a regular pace with an amplitude above the threshold value. The lower line labeled A-sense channel shows sensing the FFRW within the regular FFRW detection window with no indication in the search FFRW detection window. This indicates that the search pace was below the threshold value and did not result in atrial capture. In FIG. 9B, the upper line labeled A-pace shows application of an atrial pace with an amplitude at or above the threshold value and a regular pace with an amplitude above the threshold value. The lower line labeled A-sense channel shows sensing the FFRW within the search FFRW detection window with no indication in the regular FFRW detection window. The search pace was at or above the threshold value and was captured, so the FFRW switched from the regular FFRW detection window to the search FFRW detection window. The switch between the FFRW detection windows is easily detected and provides a clear indication that the threshold value has been reached.

The preceding specific embodiments are illustrative of the practice of the invention. It is to be understood, therefore, that other expedients known to those skilled in the art or disclosed herein, may be employed without departing from the invention or the scope of the appended claims. For example, the present invention is not limited to determining an atrial capture threshold. The present invention is also not limited to atrial capture threshold determining algorithms per se, but may find further application as a means for determining an atrial capture threshold. The present invention further includes within its scope methods and systems for determining an atrial capture threshold described above.

In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

I claim:

1. A method for detecting atrial capture, comprising:
   determining whether stable FFRW sensing is present;
   measuring a FFRW detection time if stable FFRW sensing is present;
   specifying a FFRW detection window around the FFRW detection time;
   applying an atrial pace; and
   monitoring the FFRW detection window for a FFRW in response to the atrial pace.

2. The method of claim 1, wherein determining whether stable FFRW sensing is present further comprises:
   applying atrial paces at a normal heart rate; and
   verifying FFRWs are detected in the atrium in response to the atrial paces.

3. The method of claim 2, further comprising:
   applying a predetermined number of successive atrial paces, and
   verifying the predetermined number of successive FFRWs are detected in the atrium in response to successive atrial paces.

4. The method of claim 3, wherein the predetermined number is from 5 to 20.

5. The method of claim 4, wherein the predetermined number is 10.

6. The method of claim 1, wherein the FFRW detection window is 50 msec wide and centered at an average FFRW detection time after the atrial pace.

7. The method of claim 1, further comprising:
   determining a threshold value for an atrial test variable of the atrial pace by changing the value of the atrial test variable in small increments; and
   determining the threshold value when the FFRW is no longer seen in the FFRW detection window.

8. The method of claim 7, wherein the atrial test variable is selected from the group consisting of amplitude and pulse width.

9. The method of claim 8, wherein the small increment for changing the amplitude is 0.1 to 0.5 V.

10. The method of claim 9, wherein the small increment for changing the amplitude is 0.1 V.

11. The method of claim 8, wherein the small increment for changing the pulse width is 0.05 msec.

12. The method of claim 1, further comprising:
determining a threshold value for an atrial test variable of the atrial pace by changing the value of the atrial test variable in small increments; and
determining the threshold value when the FFRW appears in the FFRW detection window.

13. The method of claim 12, wherein the atrial test variable is selected from the group consisting of amplitude and pulse width.

14. The method of claim 13, wherein the small increment for changing the amplitude is 0.1 to 0.5 V.

15. The method of claim 14, wherein the small increment for changing the amplitude is 0.1 V.

16. The method of claim 13, wherein the small increment for changing the pulse width is 0.05 msec.

17. The method of claim 1, further comprising:
specifying a search detection window at a time difference before the FFRW detection time;
applying a search pace at the time difference before the atrial pace;
determining a threshold value for an atrial test variable of the search pace by changing the value of the atrial test variable in small increments; and
determining the threshold value when the FFRW moves between the FFRW detection window and the search detection window.

18. The method of claim 17, wherein the atrial test variable is selected from the group consisting of amplitude and pulse width.

19. The method of claim 18, wherein the small increment for changing the amplitude is 0.1 to 0.5 V.

20. The method of claim 19, wherein the small increment for changing the amplitude is 0.1 V.

21. The method of claim 18, wherein the small increment for changing the pulse width is 0.05 msec.

22. The method of claim 17, wherein the search detection window is 50 msec wide and centered at an average FFRW detection time after the search pace.

23. An implantable medical system, comprising:
means for determining whether stable FFRW sensing is present;
means for measuring a FFRW detection time if stable FFRW sensing is present;
means for specifying a FFRW detection window around the FFRW detection time;
means for applying an atrial pace; and
means for monitoring the FFRW detection window for a FFRW in response to the atrial pace.

24. The system of claim 23, wherein the means for determining whether stable FFRW sensing is present further comprise:
means for applying atrial paces at a normal heart rate; and
means for verifying FFRWs are detected in the atrium in response to the atrial paces.

25. The system of claim 24, further comprising
means for applying a predetermined number of successive atrial paces, and
means for verifying the predetermined number of successive FFRWs are detected in the atrium in response to successive atrial paces.

26. The system of claim 25, wherein the predetermined number is from 5 to 20.

27. The system of claim 26, wherein the predetermined number is 10.

28. The system of claim 23, wherein the FFRW detection window is 50 msec wide and centered at an average FFRW detection time after the atrial pace.

29. The system of claim 23, further comprising:
means for determining a threshold value for an atrial test variable of the atrial pace by changing the value of the atrial test variable in small increments; and
means for determining the threshold value when the FFRW is no longer seen in the FFRW detection window.

30. The system of claim 29, wherein the atrial test variable is selected from the group consisting of amplitude and pulse width.

31. The system of claim 30, wherein the small increment for changing the amplitude is 0.1 to 0.5 V.

32. The system of claim 31, wherein the small increment for changing the amplitude is 0.1 V.

33. The system of claim 30, wherein the small increment for changing the pulse width is 0.05 msec.

34. The system of claim 23, further comprising:
means for determining a threshold value for an atrial test variable of the atrial pace by changing the value of the atrial test variable in small increments; and
means for determining the threshold value when the FFRW appears in the FFRW detection window.

35. The system of claim 34, wherein the atrial test variable is selected from the group consisting of amplitude and pulse width.

36. The system of claim 35, wherein the small increment for changing the amplitude is 0.1 to 0.5 V.

37. The system of claim 36, wherein the small increment for changing the amplitude is 0.1 V.

38. The system of claim 35, wherein the small increment for changing the pulse width is 0.05 msec.

39. The system of claim 23, further comprising:
means for specifying a search detection window at a time difference before the FFRW detection time;
means for applying a search pace at the time difference before the atrial pace;
means for determining a threshold value for an atrial test variable of the search pace by changing the value of the atrial test variable in small increments; and
means for determining the threshold value when the FFRW moves between the FFRW detection window and the search detection window.

40. The system of claim 39, wherein the atrial test variable is selected from the group consisting of amplitude and pulse width.

41. The system of claim 40, wherein the small increment for changing the amplitude is 0.1 to 0.5 V.

42. The system of claim 41, wherein the small increment for changing the amplitude is 0.1 V.

43. The system of claim 39, wherein the small increment for changing the pulse width is 0.05 msec.

44. The system of claim 39, wherein the search detection window is 50 msec wide and centered at an average FFRW detection time after the search pace.

45. A computer usable medium storing computer readable program code having a program for detecting atrial capture, comprising:
computer readable program code for determining whether stable FFRW sensing is present;

computer readable program code for measuring a FFRW detection time if stable FFRW sensing is present;

computer readable program code for specifying a FFRW detection window around the FFRW detection time;

computer readable program code for applying an atrial pace; and computer readable program code for monitoring the FFRW detection window for a FFRW in response to the atrial pace.

46. The program of claim 45, wherein the computer readable program code for determining whether stable FFRW sensing is present further comprises:

computer readable program code for applying atrial paces at a normal heart rate; and computer readable program code for verifying FFRWs are detected in the atrium in response to the atrial paces.

47. The program of claim 46, further comprising computer readable program code for applying a predetermined number of successive atrial paces, and computer readable program code for verifying the predetermined number of successive FFRWs are detected in the atrium in response to successive atrial paces.

48. The program of claim 47, wherein the predetermined number is from 5 to 20.

49. The program of claim 48, wherein the predetermined number is 10.

50. The program of claim 45, wherein the FFRW detection window is 50 msec wide and centered at an average FFRW detection time after the atrial pace.

51. The program of claim 45, further comprising:

computer readable program code for determining a threshold value for an atrial test variable of the atrial pace by changing the value of the atrial test variable in small increments; and computer readable program code for determining the threshold value when the FFRW is no longer seen in the FFRW detection window.

52. The program of claim 51, wherein the atrial test variable is selected from the group consisting of amplitude and pulse width.

53. The program of claim 52 wherein the small increment for changing the amplitude is 0.1 to 0.5 V.

54. The program of claim 53, wherein the small increment for changing the amplitude is 0.1 V.

55. The program of claim 52, wherein the small increment for changing the pulse width is 0.05 msec.

56. The program of claim 45, further comprising:

computer readable program code for determining a threshold value for an atrial test variable of the atrial pace by changing the value of the atrial test variable in small increments; and computer readable program code for determining the threshold value when the FFRW appears in the FFRW detection window.

57. The program of claim 56, wherein the atrial test variable is selected from the group consisting of amplitude and pulse width.

58. The program of claim 57, wherein the small increment for changing the amplitude is 0.1 to 0.5 V.

59. The program of claim 58, wherein the small increment for changing the amplitude is 0.1 V.

60. The program of claim 57, wherein the small increment for changing the pulse width is 0.05 msec.

61. The program of claim 45, further comprising:

computer readable program code for specifying a search detection window at a time difference before the FFRW detection time;

computer readable program code for applying a search pace at the time difference before the atrial pace;

computer readable program code for determining a threshold value for an atrial test variable of the search pace by changing the value of the atrial test variable in small increments; and computer readable program code for determining the threshold value when the FFRW moves between the FFRW detection window and the search detection window.

62. The program of claim 61, wherein the atrial test variable is selected from the group consisting of amplitude and pulse width.

63. The program of claim 62, wherein the small increment for changing the amplitude is 0.1 to 0.5 V.

64. The program of claim 63, wherein the small increment for changing the amplitude is 0.1 V.

65. The program of claim 64, wherein the small increment for changing the pulse width is 0.05 msec.

66. The program of claim 61, wherein the search detection window is 50 msec wide and centered at an average FFRW detection time after the search pace.

* * * * *